(12) United States Patent
Gesson et al.

(10) Patent No.: US 6,965,039 B2
(45) Date of Patent: Nov. 15, 2005

(54) 7-CARBOXY-FLAVONE DERIVATIVES PREPARATION METHOD AND THERAPEUTIC USE

(75) Inventors: Jean-Pierre Gesson, Montamise (FR); Nadia Fonteneau, Villebois-Lavalette (FR); Martine Mondon, Poitiers (FR); Suzy Charbit, Creteil (FR); Hervé Ficheux, Nogent-sur-Marne (FR); Francois Schutze, Saint-Nom-la-Breteche (FR)

(73) Assignee: Negma-Lerads, Toussus le Noble (FR)

( * ) Notice: Subject to any disclaimer, the term of this patent is extended or adjusted under 35 U.S.C. 154(b) by 14 days.

(21) Appl. No.: 10/398,187

(22) PCT Filed: Oct. 5, 2001

(86) PCT No.: PCT/FR01/03075

§ 371 (c)(1),
(2), (4) Date: Oct. 3, 2003

(87) PCT Pub. No.: WO02/28851

PCT Pub. Date: Apr. 11, 2002

(65) Prior Publication Data

US 2004/0059136 A1 Mar. 25, 2004

(30) Foreign Application Priority Data

Oct. 6, 2000 (FR) .......................................... 00 12846

(51) Int. Cl.⁷ ............................................ C07D 311/30
(52) U.S. Cl. ...................................................... 549/403
(58) Field of Search ......................................... 549/403

(56) References Cited

U.S. PATENT DOCUMENTS 4,157,334 A 6/1979 Doria et al.
5,399,584 A 3/1995 Ares et al.

FOREIGN PATENT DOCUMENTS

| EP | 0 237 986 A2 | 9/1987 |
| EP | 0 290 915 A2 | 11/1988 |
| FR | 2 543 140 A1 | 9/1984 |
| FR | 2 689 127 A1 | 10/1993 |

OTHER PUBLICATIONS

Zwangstra, M.E., et al., *J. Med. Chemistry*, 41:1428–1438 (1998).
Abad, M.J., et al., *J. Nat. Prod.* 56(7):1164–1173 (1993).
Silvan, A.M., et al., *Planta Med.* 64:200–203 (1998).
Adam, W., et al., *J. Org. Chem.* 56:7292–7297 (1991).
Moriarty, R.M., et al., *J. Heterocycl. Chem.* 22:583 (1985).
Schindler, R., et al., *Blood* 75:40–47 (1990).
Honda, M., et al., *Diabetes Res.* 14:43–46 (1990).
Bennett, C.F., et al., *Biochem. J.* 289:33–39 (1993).
Lorico, A., et al., *Biochem. Pharmacol.* 35:2443–2445 (1986).
Tayeh, M.A., *J. Biol. Chem.* 264:19654–19658 (1989).
Silvan, Ana Maria, "Effects of Compounds Extracted From Tanacetum Microphyllum", Planta Medica, vol. 64, No. 3, (1998), pp. 200–203.
Abad, M.J., et al., "Anti–Inflammatory Activity of Two Flavonoids From Tanacetum Microphyllum", Journal of Natural Products, vol. 56, No. 7, Jul. 1993, pp. 1164–1167.

*Primary Examiner*—Taofiq Solola
(74) *Attorney, Agent, or Firm*—Burns, Doane, Swecker & Mathis, L.L.P.

(57) ABSTRACT

The invention concerns novel flavone and isoflavone derivatives of formulae (Ia) and (Ib) wherein: X represents a group of formula —COOR, or —PO(OR)$_2$; R represents a hydrogen atom or an alkaline or alkaline-earth metal, or a lower alkyl group; $R_1$ represents a hydroxy group, a lower alkoxy group or an acyloxy group; $R_2$ and $R_3$, identical or different, represent a hydrogen or halogen atom, or a trifluoromethyl group, a trichloromethyl group, a hydroxy group, an alkoxy group or an acyloxy group comprising 1 to 5 carbon atoms, or $R_2$ and $R_3$ can combine to form an alkylene dioxy group. The invention is useful for rheumatic diseases.

19 Claims, No Drawings

7-CARBOXY-FLAVONE DERIVATIVES PREPARATION METHOD AND THERAPEUTIC USE

BACKGROUND OF THE INVENTION

1. Field of the Invention

The present invention relates to novel flavone and isoflavone derivatives of use therapeutically and more particularly to novel flavone derivatives carrying an acid group, to their therapeutic application in the treatment of rheumatic diseases, and to a process for their preparation.

2. Description of the Related Art

A large number of variously substituted flavone derivatives have been disclosed in the literature, as have their pharmacological properties of use in numerous therapeutic applications, such as, for example, the treatment of asthma, of inflammatory diseases, of gastrointestinal conditions, of allergies or of certain cancerous tumors.

For example, U.S. Pat. No. 5,399,584 discloses flavone derivatives which can be used for protecting the wall of the gastrointestinal tract in complementing a treatment by means of nonsteroidal anti-inflammatories. Patent EP 290 915 discloses flavone-3-carboxylic acids presented as having a pharmacological activity in which the formation of oxygen radicals in the cells is inhibited, making it possible to envisage their use as anti-inflammatory medicaments. Flavone-4'-carboxylic acids substituted in the 7 position by an amide or sulfonamide group, of use in the treatment of diabetic neuropathies, are disclosed in patent FR 2 543 140. Patent EP 237 986 discloses other flavone derivatives substituted on the phenyl ring by a carboxylic acid or ester group which exhibit antitumor properties.

Some carboxyflavones capable of exhibiting a useful activity in the treatment of asthma have been described by M. E. Zwangstra et al., *J. Med. Chemistry*, (1998) 41, 1428–1438. Other flavone derivatives, such as, for example, flavone-6-carboxylic acids, in particular 6-carboxy-2'-isopropoxyflavone, exhibiting anti-allergizing properties and a spasmolytic activity, are disclosed in U.S. Pat. No. 4,157,334. Patent FR 2 689 127 discloses di(t-butyl)-3',5'-4'-hydroxyflavones [sic] capable of being used in the treatment of dyslipidemias, of atherosclerosis and of ischemic cardiopathies. Centaureidin, or 5,7,3'-trihydroxy-3,6,4'-trimethoxy-flavone, is a flavonoid isolated from *Tanacetum microphyllum*, described by M. J. Abad et al., *J. Nat. Prod.*, Vol. 56, No. 7, pp. 1164–1173 (1993), exhibiting anti-inflammatory properties comparable with that [sic] of phenylbutazone, confirmed experimentally on the mouse. The same anti-inflammatory activity has been confirmed with regard to the metabolism of arachidonic acid (release of prostaglandin $E_2$ and leukotriene $C_4$) and has been described in *Planta Med.*, Vol. 64, pp. 200–203 (1998). However, no inhibiting effect on the cytokines involved in the inflammatory process of rheumatic diseases has been observed.

In the field of medicaments intended for the treatment of certain pathologies, such as arthrosis, rhein derivatives, in particular diacerhein, have been described as being particularly effective at high doses. However, one of the disadvantages related to the use of these compounds is that they can exhibit, in some subjects, troublesome side effects according to the dosage used and in particular a laxative effect. It is therefore desirable to be able to have available anti-inflammatory medicaments having an at least equal therapeutic effectiveness which are devoid of the side effects intrinsic to rheins.

SUMMARY OF THE INVENTION

A subject matter of the present invention is novel flavone derivatives, and more particularly flavone and isoflavone derivatives carrying an acid group in the 7 position, exhibiting advantageous anti-inflammatory properties which allow them to be used as medicaments in the treatment of certain rheumatic diseases, such as arthrosis or rheumatoid arthritis.

Another subject matter of the invention is a process for the preparation of flavone and isoflavone derivatives carrying an acid group in the 7 position starting from products which are readily accessible or available commercially.

Finally, a subject matter of the invention is the therapeutic application of the novel flavone and isoflavone derivatives carrying an acid group in the 7 position, more particularly in the treatment of rheumatic diseases in human and veterinary therapy, and the use of said flavone and isoflavone derivatives in the preparation of a medicament for the treatment of rheumatic diseases, such as arthrosis or rheumatoid arthritis.

DETAILED DESCRIPTION OF THE PREFERRED EMBODIMENTS

The novel flavone and isoflavone derivatives in accordance with the present invention can be represented by the general formulae (Ia) and (Ib) below:

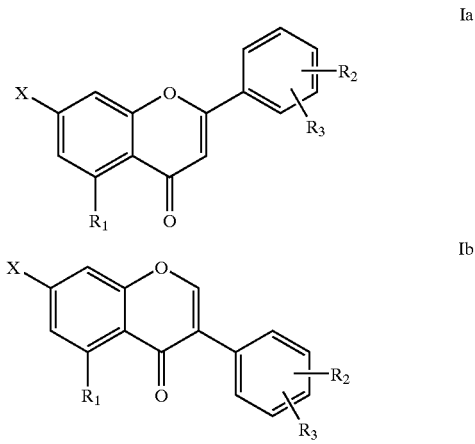

in which X represents a group of formula —COOR or —PO(OR)$_2$, R represents a hydrogen atom or an alkali metal or alkaline earth metal atom, or a linear or branched lower alkyl group comprising 1 to 5 carbon atoms, $R_1$ represents a hydroxyl group, a linear or branched lower alkoxy group comprising 1 to 5 carbon atoms or an acyloxy group comprising 1 to 5 carbon atoms, $R_2$ and $R_3$, which are identical or different, represent a hydrogen or halogen atom or a trifluoromethyl group, a trichloromethyl group, a hydroxyl group, a linear or branched alkoxy group comprising 1 to 5 carbon atoms or an acyloxy group comprising 1 to 5 carbon atoms, or $R_2$ and $R_3$ can combine to form an alkylenedioxy group.

In the above formulae (Ia) and (Ib), X preferably represents a carboxylic or phosphoric acid group or an ester in which R is a methyl or ethyl group, and $R_1$ preferably represents a hydroxyl, acetoxy or methoxy group.

$R_2$ preferably represents a hydrogen, chlorine or fluorine atom, a trifluoromethyl group, a carboxyl group or an alkoxy group, and in particular a methoxy group, and $R_3$ is preferably a hydrogen atom. The substituent represented by $R_2$ is preferably situated in the 4' position of the phenyl ring. $R_2$ and R₃ can combine in order together to form an ethylenedioxy or methylenedioxy group.

When the X substituent is [lacuna] carboxylic acid derivative, it preferably represents the —COOH or —COOCH₃ group. When it is a phosphoric acid derivative, it preferably represents a —PO(OH)₂ or —PO(OCH₃)₂ group.

The derivatives of the invention can be provided in particular in the form of carboxylic acid salts having one or other of the above formulae (Ia) and (Ib) where X is a —COOR group, R being more particularly a sodium atom or a potassium atom.

The novel flavone derivatives represented by the above formula (Ia) can be prepared from the 5,7-dihydroxyflavones represented by the general formula (IIa) below

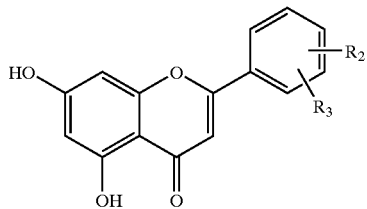

IIa in which the R₂ and R₃ substituents have the same meanings as in the formula (Ia), by reaction with a trifluoroalkanesulfonic anhydride in the presence of a nonprotic base in an appropriate solvent, then reaction with an acid chloride or an acid anhydride in the presence of a nonprotic base, to form the derivatives of formula (IIIa) below

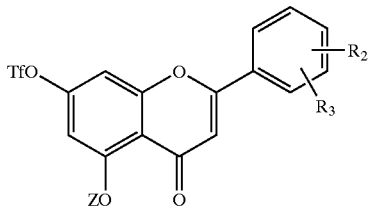

IIIa in which Z is a pivaloyl, methoxymethyl or trialkylsilyl group, then a carbonylation is carried out in the presence of a palladium-based catalyst, a phosphorus-comprising ligand and an alcohol, in an appropriate solvent, and the protective groups in the 5 and 7 position [sic] are removed.

Deprotection can be carried out in a known way, depending on the protective groups used. For example, deprotection can be carried out in a basic medium for ester functional groups, in the presence of potassium fluoride or tetrabutylammonium fluoride for a trimethylsilyl ester, or in an acidic medium for a methoxymethyl group.

Isoflavone derivatives of formula (Ib) are prepared analogously from the corresponding 5,7-dihydroxy-isoflavones represented by the formula (IIb) below,

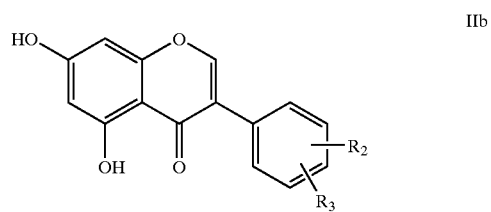

IIb in which the R₂ and R₃ substituents have the same meanings as in the formula (Ib), in order to obtain the intermediate of formula (IIIb)

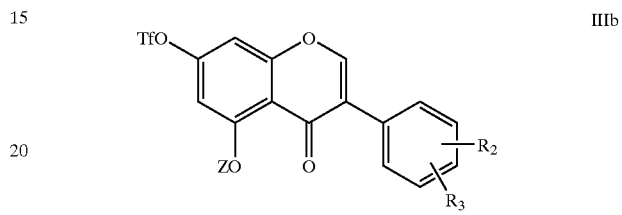

IIIb in which Z, R₂ and R₃ have the same meanings as above, and then treatment via the same reaction scheme.

The reaction of the trifluoroalkanesulfonic anhydride with the dihydroxyflavone of formula (II) is carried out in the presence of a nonprotic base which can advantageously be chosen from pyridine and triethylamine and it is preferably carried out in a solvent, such as dichloromethane.

The trifluoroalkanesulfonic anhydride used in the process according to the invention is preferably trifluoromethanesulfonic anhydride. The chloride used in the reaction for the preparation of the derivatives of formula (IIIa) can be chosen from pivaloyl chloride, methoxymethyl chloride or else a trialkylsilyl chloride, in the presence of a nonprotic base, such as pyridine.

The palladium-based catalyst used in the carbonylation stage of the process according to the invention can, for example, be Pd(OAc)₂ in the presence of carbon monoxide. The phosphorus-comprising derivative can, for example, be 1,3-bis(diphenylphosphino)propane and the alcohol can, for example, be methanol or 2-(trimethylsilyl)ethanol. The solvent used in this stage is preferably DMF or DMSO.

It may be observed that the starting flavones represented by the general formula (IIa) might be used for the preparation of 3,5,7-trihydroxyflavones, the hydroxyl group of which in the 7 position would behave like the corresponding group in the 5,7-dihydroxyflavones, whereas the hydroxyl group of which in the 3 position would behave like the group in the 5 position. These trihydroxyflavones can be prepared from the corresponding dihydroxyflavones comprising a hydrogen atom in the 3 position by reaction with dimethyldioxirane in acetone, according to the method of W. Adam et al., *J. Org. Chem.*, (1991) 56, 7292–7297, or by reaction with iodosylphenyl diacetate according to the method of R. M. Moriarty et al., *J. Heterocycl. Chem.*, (1985) 22, 583. In contrast, in the isoflavone series, only the 5,7-dihydroxy derivatives are stable, unlike the highly unstable 2,5,7-trihydroxyflavones [sic].

The experiments carried out on the derivatives of the present invention have demonstrated advantageous pharmacological properties and in particular a significant inhibiting effect on the production of inflammatory cytokines involved in rheumatic disease. These results make it possible to envisage their use in the treatment of arthrosis and of rheumatoid arthritis, and very particularly of arthrosis.

Furthermore, the tests carried out have shown that the 7-carboxyflavone and 7-carboxyisoflavone derivatives according to the present invention are potentially more active than the reference anti-inflammatories, such as rhein derivatives, in particular diacerhein (rhein being the active metabolite of diacerhein), commonly used in human therapy in the treatment of arthrosis. On the other hand, they do not exhibit the laxative side effects inherent in these known medicaments. These results are doubtless due to the fact that the flavone derivatives do not possess the quinone ring regarded as responsible for the laxative effect, but retain the inhibiting properties with respect to interleukin 1 and other cytokines.

The inhibiting activity on the secretion of inflammatory cytokines of the compounds of the invention was tested in vitro, more particularly on the secretion of IL-1 (interleukin 1) and on IL-6 and TNFα (tumor necrosis factor), which are the main cytokines related to the arthrotic process.

The tests on these three cytokines were carried out on PBMC (Peripheral Blood Mononuclear Cells) cells according to the method of Schindler (R. Schindler et al., *Blood*, (1990) 75, 40–47) using cycloheximide (IL-1) and dexamethasone (IL-6, TNFα) as reference products.

The effect of the derivatives of the invention on the secretion of prostaglandins ($PGE_2$), which increase articular inflammation, and of leukotriene ($LTB_4$) was measured on differentiated HL-60 cells using the methods of Honda (M. Honda et al., *Diabetes Res.*, (1990) 14, 43–46) and of Bennett (C. F. Bennett et al., *Biochem. J.*, (1993) 289, 33–39), respectively, using indomethacin and nordihydroguaiaretic acid as reference products.

The study of the secretion of oxygen, making it possible to evaluate the state of stress of the cell, was carried out on HL-60 cells according to the method of Lorico (A. Lorico et al., *Biochem. Pharmacol.*, (1986) 35, 2443–2445).

Tests were also carried out on the stimulation of NO synthase, given that interleukin 1 increases the production of NO by stimulation of NO synthase (NOS). These tests were carried out according to the method of Tayeh (M. A. Tayeh et al., *J. Biol. Chem.*, (1989) 264, 19654–19658).

The results of the tests carried out with the flavone derivatives of the invention described in examples 1, 4 and 6 above [sic] are combined in the following table. The tests were carried out in duplicate, at concentrations of 1 and 10 $\mu M$. The results are expressed as percentage of inhibition.

| | | Results | | |
|---|---|---|---|---|
| Example | $\mu M$ | IL1β | IL6 | TNFα |
| 1 | 10 | 96 | 98 | 32 |
| | 1 | 15 | 50 | 61 |
| 4 | 1 | <10 | 56 | na |
| 6 | 10 | 72 | 100 | na | na: result not available (test not carried out).

These results show that the flavone derivatives according to the present invention exert significant inhibiting effects on IL-1 and IL-6. The derivative of example 4 furthermore exhibits the distinctive feature of stimulating the secretion of prostaglandins. The percentages of inhibition are very high with respect to those observed with reference antiarthrotic inflammatories, which are rhein and diacerhein.

The toxicological studies carried out have shown that the derivatives of the invention have a low toxicity at the doses normally used in treatments.

The pharmacological properties of the flavone and isoflavone derivatives according to the present invention, combined with their low toxicity, show that they can advantageously be used in the treatment of rheumatic diseases and very particularly of arthrosis. They can be presented in the form of esters or of salts, as a mixture, if appropriate, with pharmaceutically acceptable carriers or excipients.

The flavone derivatives in accordance with the present invention can be administered in the forms usual in the pharmaceutical art, and for example in the form of tablets, capsules, including gelatin capsules, injectable solutions, solutions to be taken orally, transdermal gels, and the like, suited to the administration route chosen, that is to say generally by the oral, parenteral or transdermal route. The working dosage is adjusted according to the seriousness of the condition to be treated, the age and the weight of the patient, and the method of administration used. The single doses are generally between 10 mg and 5 g per day, taken one to three times.

The following examples describe the preparation of derivatives in accordance with the present invention, given without implied limitation.

EXAMPLE 1

5-Hydroxy-2-phenyl-4-oxo-4H-chromene-7-carboxylic acid 12.7 ml of pyridine and then 6.6 ml of trifluoromethanesulfonic anhydride are added to a solution of 200 ml of dichloromethane comprising 10 g of 5,7-dihydroxyflavone while maintaining the temperature at 0° C. After reacting for approximately 3 h at 0° C., the reaction mixture is neutralized with a 1N hydrochloric acid solution and then extracted with dichloromethane.

After evaporation of the solvent, 13.9 g (92% yield) of 7-trifluoromethanesulfonyloxy-5-hydroxy-2-phenyl-4-oxo-4H-chromene are recovered in the form of a white powder, the chemical structure of which is confirmed by chromatography and infrared spectrum, corroborated by NMR and mass spectrum.

Rf=0.58 (AcOEt/PE=30/70)

I.R. ($cm^{-1}$): 1655 (C=O), 1620 (C=C), 1436 (S=O).

0.16 ml of pivaloyl chloride is added to the product obtained as indicated above (330 mg) in solution in 4 ml of pyridine at 0° C. and reaction is allowed to take place for approximately 48 h while maintaining the temperature at 0° C.

After separating by flash chromatography (eluents AcOEt/EP=5/95 to 10/90), 7-trifluoromethane-sulfonyloxy-2-phenyl-5-pivaloyloxy-4-oxo-4H-chromene (95% yield) is obtained in the form of a white powder exhibiting a melting point M.p.=126–128° C.

Rf=0.65 (AcOEt/EP =10/90)

I.R. ($cm^{-1}$): 1752 (C=O ester), 1657 (C=O), 1614 (C=C), 1427 (S=O).

The above derivative (200 mg) is subsequently mixed with 8.7 mg of 1,3-bis(diphenylphosphino)propane and 4.7 mg of Pd(OAc)$_2$ under an atmosphere of carbon monoxide in a three-necked round-bottomed flask and is treated [lacuna] 0.2 ml of 2-(trimethylsilyl)ethanol in the presence of 0.12 ml of triethylamine and 0.9 ml of DMSO. The mixture is stirred at 70° C. for approximately 3 h, extracted with dichloromethane and washed with a 1N hydrochloric acid solution.

After separating by flash chromatography (eluents AcOEt/PE=5/95 to 10/90), 181 mg of 2-(trimethylsilyl)ethyl 2-phenyl-5-pivaloyloxy-4-oxo-4H-chromene-7-carboxylate (91% yield) are obtained in the form of white crystals exhibiting a melting point M.p.=205° C.

Rf=0.26 (CH$_2$Cl$_2$/MeOH=97/3).

202 mg of tetrabutylammonium fluoride, in solution in 2 ml of tetrahydrofuran, are added to the above carboxylate (180 mg) at 0° C., reaction is then allowed to take place at ambient temperature for approximately 19 h and a 1N sodium hydroxide solution (4.1 ml) is added. After 72 h, the mixture is hydrolyzed with a 1N hydrochloric acid solution and then extracted with ethyl acetate.

The 5-hydroxy-2-phenyl-4-oxo-4H-chromene-7-carboxylic acid thus obtained, after purification by recrystallization from a methanol/chloroform (1-9) mixture, is provided in the form of a yellow powder.

Melting point M.p.=270° C. (decomposition).

Rf=0.24 (CH$_2$Cl$_2$/MeOH=95/5).

I.R. (cm$^{-1}$): 1724 (COOH), 1656 (C=O), 1614 (C=C).

$^1$H NMR (CDCl$_3$/CD$_3$OD=9/1) δ ppm: 6.74 (s, 1H, H-3), 7.40 and 7.66 (2s, 2H, H-6 and H-8), 7.48–7.51 (m, 3H, H-3' and H-4'), 7.88 (d, 2H, J=6.4 Hz, H-2').

$^{13}$C NMR (DMSO [sic]) δ ppm: 106.4, 108.9, 111.3 and 112.8 (C-3, C-8, C-6 and C-4a), 127.1 (C-2'), 129.5 (C-3'), 130.6 (C-1'), 132.9 (C-4'), 137.6 (C-7), 156.0, 160.1, 165.1 and 166.1 (C-5, C-2, C-8a and COOH), 183.3 (C-4).

EXAMPLE 2

7-Dimethoxyphosphoryl-5-hydroxy-2-phenyl-4-oxo-4H-chromene

7-Trifluoromethanesulfonyloxy-2-phenyl-5-pivaloyloxy-4-oxo-4H-chromene (500 mg), a synthetic intermediate obtained in example 1, is treated with 0.12 ml of dimethyl phosphite in the presence of 0.24 ml of diisopropylethylamine and of 61 mg of tetrakis(triphenylphosphine) palladium in solution in 2.5 ml of acetonitrile.

After heating at 70° C. for 7 h, the reaction mixture is neutralized with a 1N hydrochloric acid solution and then extracted with dichloromethane.

After separating by flash chromatography (eluents AcOEt/PE=5/95 to 50/50), 383 mg of 7-dimethoxyphosphoryl-2-phenyl-5-pivaloyloxy-4-oxo-4H-chromene (84% yield) are obtained in the form of a white powder exhibiting a melting point M.p.=165–167° C.

The above derivative is added to a solution of sodium hydroxide (5 ml), of water (10 ml) and of methanol (10 ml). After reacting at ambient temperature for 23 h, the reaction mixture is acidified with a 1N hydrochloric acid solution. The precipitate formed is washed with water. After recrystallizing from a methanol/chloroform mixture, 7-dimethoxyphosphoryl-5-hydroxy-2-phenyl-4-oxo-4H-chromene is obtained with a yield of 90% in the form of a yellow precipitate.

Melting point M.p.=219° C.

Rf=0.25 (CH$_2$Cl$_2$/MeOH=70/30).

EXAMPLE 3

7-Dihydroxyphosphoryl-5-hydroxy-2-phenyl-4-oxo-4H-chromene 0.55 ml of bromotrimethylsilane is added to the product from example 2 in solution in 13 ml of dichloromethane. After reacting at ambient temperature for 21 h, the solvent is evaporated.

After recrystallizing from an ethanol/chloroform mixture, 7-dihydroxyphosphoryl-5-hydroxy-2-phenyl-4-oxo-4H-chromene is obtained in the form of a yellow powder with a yield of 68%.

Melting point M.p.=293–296° C. (decomposition).

I.R. (cm$^{-1}$): 1655 (C=O), 1616 (C=C), 1261 (P=O).

$^1$H NMR (DMSO [sic]) δ ppm: 6.98 and 7.44 (2s, 2H, J=13.5 Hz, H-6 and H-8), 7.16 (s, 1H, H-3), 7.59–7.65 (m, 3H, H-3' and H-4'), 8.15 (d, 2H, J=6.9 Hz, H-2'), 12.63 (s, OH).

$^{13}$C NMR (DMSO [sic]) δ ppm: 107.7 (C-3), 110.8 (C-4a), 111.3 and 113.9 (J=9 Hz, C-6 and C-8), 128.4 (C-2'), 130.9 (C-3'), 132.1 (C-1'), 134.2 (C-4'), 156.9 and 161.1 (J=20 Hz, C-5, C-2, C-8a), 166.3 (C-2), 183.2 (C-4).

EXAMPLE 4

5-Hydroxy-0.2-(4'-methoxyphenyl)-4-oxo-4H-chromene-7-carboxylic acid

The preparation is carried out as shown in example 1 under the same operating conditions, the starting 5,7-dihydroxyflavone being replaced with (4'-methoxyphenyl)-5,7-dihydroxyflavone [sic].

2-(Trimethylsilyl)ethyl 2-(4'-methoxyphenyl)-5-pivaloyoxy-4-oxo-4H-chromene-7-carboxylate is thus obtained, which product is treated under the same conditions as in example 1 to provide 5-hydroxy-2-(4'-methyoxyphenyl)-4-oxo-4H-chromene-7-carboxylic acid.

Melting point M.p.=277–278° C.

Rf=0.53 (CH$_2$Cl$_2$/MeOH=90/10).

EXAMPLE 5

5-Hydroxy-3-(4'-methoxyphenyl)-4-oxo-4H-chromene-7-carboxylic acid

This derivative is obtained as in the preceding example, the starting flavone being replaced with the corresponding isoflavone.

5-Hydroxy-3-(4'-methoxyphenyl)-4-oxo-4H-chromene-7-carboxylic acid is thus obtained.

Rf=0.36 (CH$_2$Cl$_2$/MeOH=90/10)

I.R. (cm$^{-1}$): 1705 (COOH), 1653 (C=O), 1611 and 1583 (C=C).

$^1$H NMR (DMSO [sic]) δ ppm: 3?87 [sic] (s, 3H, CH$_3$O—), 7.09 (s, 1H, H-3), 7.11 (d, 2H, H-6 and H-8), 8.113 (d, 2H, J=8.9 Hz, H-2').

13C NMR (DMSO [sic]) δ ppm: 55.9 (CH$_3$), 104.6, 108.7 and 111.1 (C-3, C-6 and C-8), 112.5 (C-4a), 114.9 (C-3'), 122.6 (C-1'), 129.1 (C-2 ), 137.5 (C-7), 155.8, 160.0, 163.0, 165.2 and 166.1 (C-2, C-4', C-5, C-8a and COOH), 183.0 (C-4).

EXAMPLE 6

5-Hydroxy-2-(4'-trifluoromethylphenyl)-4-oxo-4H-chromene-7-carboxylic acid

The preparation is carried out as in example 1 under the same operating conditions, the starting 5,7-dihydroxyflavone being replaced with (4'-trifluoromethylphenyl)-5,7-di-hydroxyflavone [sic].

5-Hydroxy-3-(4'-trifluoromethylphenyl)-4-oxo-4H-chromene-7-carboxylic acid is thus obtained.

Melting point M.p.=278° C. (decomposition)

Rf=0.18 (CH$_2$Cl$_2$/MeOH=90/10).

$^1$H NMR (CDCl$_3$/CD$_3$OD=9/1) δ ppm: 6.88 (s, 1H, H-3), 7.49 and 7.74 (2d, 2H, J=1.2 Hz, H-6 and H-8), 7.82 (d, 2H, J=8.3 Hz, H-3'), 8.09 (d, 2H, J=8.2 Hz, H-2').

$^{13}$C NMR (DMSO [sic]) δ ppm: 108.5, 109.6, 112.1 and 113.4 (C-3, C-4a, C-6 and C-8), 124.7 (q, J=271.0 Hz, CF$_3$), 126.97 (q, J=3.6 Hz, C-3'), 128.6 (C-2'), 132.8 (q, J=32.0 Hz, C-4'), 135.2 (C-7), 138.8 (C-1), 156.6, 160.7, 163.9 and 166.8 (C-2, C-5, C-8a and COOH), 184.0 (C-4).

What is claimed is:

1. Flavone and isoflavone derivatives represented by the following general formulae (Ia) and (Ib):

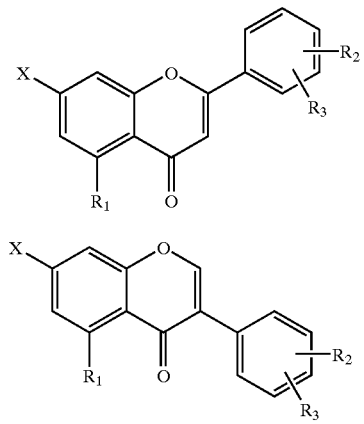

in which X represents a group of formula —COOR or —PO(OR)$_2$; R represents a hydrogen atom, an alkali metal or alkaline earth metal atom, or a linear or branched lower alkyl group having 1 to 5 carbon atoms; R$_1$ represents a hydroxyl group, a linear or branched lower alkoxy group having 1 to 5 carbon atoms or an acyloxy group having 1 to 5 carbon atoms; R$_2$ and R$_3$, which are identical or different, represent a hydrogen atom, a halogen atom, a trifluoromethyl group, a trichloromethyl group, a hydroxyl group, a linear or branched alkoxy group having 1 to 5 carbon atoms or an acyloxy group having 1 to 5 carbon atoms, or R$_2$ and R$_3$ together with the carbon atoms to which they are attached combine to form an alkylenedioxy group.

2. Derivatives according to claim 1, wherein X represents a carboxylic or phosphoric acid group or an ester in which R is a methyl group, and R$_1$ represents hydroxyl, acetoxy or methoxy group.

3. Derivatives according to claim 1, wherein R$_2$ represents a hydrogen atom, a fluorine atom, a trifluoromethyl group, a carboxyl group or an alkoxy group and R$_3$ is a hydrogen atom, or R$_2$ and R$_3$ together form an ethylenedioxy or methylenedioxy group.

4. Derivatives according to claim 2, wherein X is a —COOH group, R$_1$ is a hydroxyl group and R$_2$ represents a hydrogen atom, a trifluoromethyl group or a methoxy group situated in the 4' position of the phenyl ring.

5. Derivatives according to claim 1, wherein X is a —COOR group where R is a sodium atom or a potassium atom.

6. Derivatives according to claim 1, wherein the derivatives are selected from the group consisting of 5-hydroxy-2-phenyl-4-oxo-4H-chromene-7-carboxylic acid, 7-dihydroxyphosphoryl-5-hydroxy-2-phenyl-4-oxo-4H-chromene, 5-hydroxy-2-(4'-methoxyphenyl)-4-oxo-4H-chromene-7-carboxylic acid and 5-hydroxy-2-(4'-trifluoromethylphenyl)-4-oxo-4H-chromene-7-carboxylic acid.

7. Process for the preparation of flavone and isoflavone derivatives represented by the general formulae (Ia) and (Ib) according to claim 1, wherein a 5,7-dihydroxyflavone, represented by the following general formula (IIa) or (IIb)

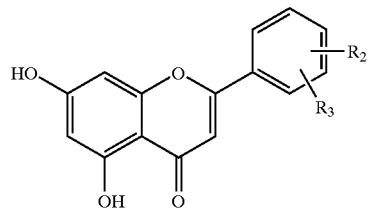

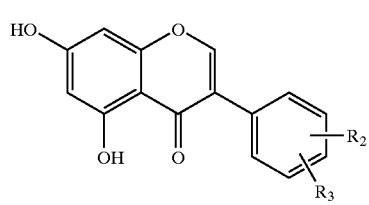

in which R$_2$ and R$_3$, which are identical or different, represent a hydrogen atom, a halogen atom, a trifluoromethyl group, a trichloromethyl group, a hydroxyl group, a linear or branched alkoxy group of 1 to 5 carbon atoms or an acyloxy group of 1 to 5 carbon atoms, or R$_2$ and R$_3$ together with the carbon atoms to which they are attached combine to form an alkylenedioxy group, is reacted with a trifluoroalkanesulfonic anhydride in the presence of a nonprotic base in an appropriate solvent, then an acid chloride or an acid anhydride is reacted in the presence of a nonprotic base, to form the derivatives of formula (IIIa) or (IIIb) below

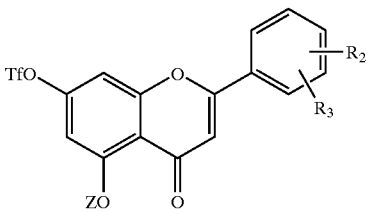

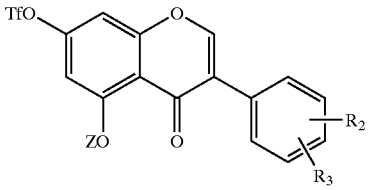

in which Z is a pivaloyl, methoxymethyl or trialkylsilyl group, then a carbonylation is carried out in the presence of a palladium-based catalyst, a phosphorus-comprising ligand and an alcohol, in appropriate solvent, and the protective groups in the 5 and 7 position are removed to provide the flavone and isoflavone derivatives of general formulae (Ia) and (Ib) according to claim 1.

8. Process according to claim 7, wherein chloride is pivaloyl chloride, methoxymethyl chloride or a trialkylsilyl chloride.

9. Process according to claim 7, wherein the nonprotic base is pyridine or triethylamine.

10. Process according to claim 7, wherein the carbonylation is carried out in the presence of a palladium-based catalyst composed of Pd(OAc)$_2$ in the presence of carbon monoxide, the phosphorus-comprising ligand is 1,3-bis(diphenyl-phosphino)propane and the alcohol is methanol or 2-(trimethylsilyl)ethanol.

11. Process according to claim 10, wherein carbonylation reaction is carried out in a solvent selected from the group consisting of DMF and DMSO.

12. Pharmaceutical composition for use in human and veterinary therapy comprising a flavone or isoflavone derivative according to claim 1 and one or more pharmaceutically acceptable excipients or carriers.

13. A method for treatment of rheumatic diseases in a subject in need thereof comprising administering to the subject a therapeutically effective amount of a flavone or isoflavone derivative according to claim 1.

14. Derivatives according to claim 2, wherein $R_2$ represents a hydrogen atom, a fluorine atom, a trifluoromethyl group, a carboxyl group or an alkoxy group and $R_3$ is a hydrogen atom, or $R_2$ and $R_3$ together form an ethylenedioxy or methylenedioxy group.

15. Derivatives according to claim 3, wherein X is a —COOH group, $R_1$ is a hydroxyl group and $R_2$ represents a hydrogen atom, a trifluoromethyl group or a methoxy group situated in the 4' position of the phenyl ring.

16. Process according to claim 8, wherein the nonprotic base is chosen from pyridine and triethylamine.

17. Pharmaceutical composition for use in human and veterinary therapy comprising a flavone or isoflavone derivative according to claim 2 and one or more pharmaceutically acceptable excipients or carriers.

18. Pharmaceutical composition for use in human and veterinary therapy comprising a flavone or isoflavone derivative according to claim 3 and one or more pharmaceutically acceptable excipients or carriers.

19. Derivatives according to claim 1, wherein $R_3$ is a hydrogen atom and $R_2$ is a hydrogen atom, a halogen atom, a trifluoromethyl group, a trichloromethyl group, a hydroxyl group, a linear or branched alkoxy group having 1 to 5 carbon atoms or an acyloxy group having 1 to 5 carbon atoms, wherein $R_2$ is situated in the 4' position of the phenyl ring.

* * * * *